(12) United States Patent
Nishio

(10) Patent No.: US 6,234,630 B1
(45) Date of Patent: May 22, 2001

(54) CORNEAL ENDOTHELIAL CELL MEASURING INSTRUMENT

(75) Inventor: Kouji Nishio, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 09/465,273

(22) Filed: Dec. 17, 1999

(30) Foreign Application Priority Data

Dec. 17, 1998 (JP) .................................................. 10-359397

(51) Int. Cl.⁷ ........................................................ A61B 3/14
(52) U.S. Cl. ............................................................ 351/206
(58) Field of Search .................................. 351/200, 205, 351/206, 221, 222; 606/4, 5

(56) References Cited

U.S. PATENT DOCUMENTS 4,340,281 * 7/1982 McIntyre ............................. 351/205
5,436,679 * 7/1995 Ohtsuka et al. ...................... 351/206

* cited by examiner

Primary Examiner—George Manuel
(74) Attorney, Agent, or Firm—Oblon, Spivak, McClelland, Maier & Neustadt, P.C.

(57) ABSTRACT

A corneal endothelial cell measuring instrument comprises a monitor for displaying a corneal endothelial cell image picked up, an input device for marking the centers of cell images in the corneal endothelial cell image displayed on the screen of the monitor, a processor for determining the coordinate value of the marked centers, forming a closed curve formed by connecting the plurality of the marked centers, calculating the area of a region enclosed by the closed curve and calculating cell density, i.e., the number of cells per unit area, from the number of the centers on the closed curve and the number of the centers inside the closed curve.

4 Claims, 4 Drawing Sheets

FIG. 4(a) (PRIOR ART)
FIG. 4(b) (PRIOR ART)
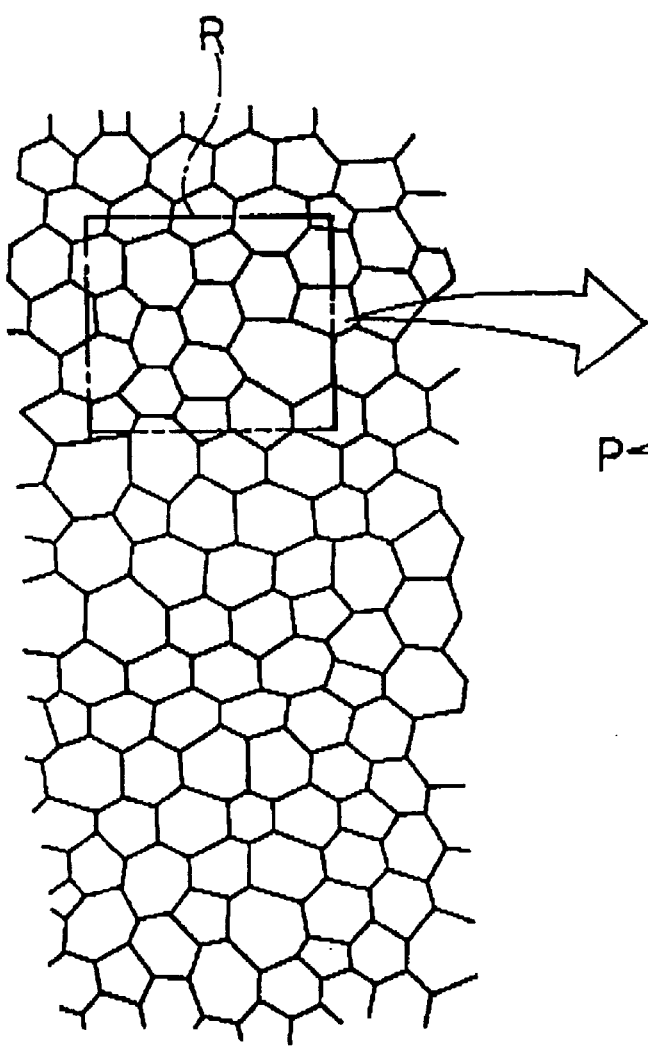
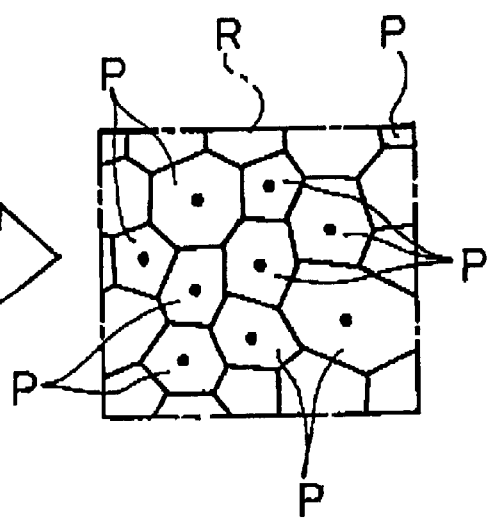

CORNEAL ENDOTHELIAL CELL MEASURING INSTRUMENT

BACKGROUND OF THE INVENTION

1. Field of the Invention

The present invention relates to a corneal endothelial cell measuring instrument for measuring cell density in a corneal endothelial cell image taken by using a specular microscope or the like.

2. Description of the Related Art

There are many kinds of methods of measuring the characteristics of corneal endothelial cells. A grid method is one of those known methods. As shown in FIGS. 4(a) and 4(b), in the grid method, a portion of a cell image is surrounded by a rectangle R of an optional size, then, the number N of cells included in the rectangle R are counted, and further, the number N of cells are divided by the area S of the rectangle R to determine a cell density CD. More specifically, when counting the number N of cells included in the rectangle R, the number of one cell entirely included in the rectangle R (i.e., nine cells P with a dot marked at their center in FIG. 4(b)) is counted as 1.0 respectively, and the number of one cell partly included in the rectangle R is counted as 0.5 respectively, regardless of the size of the portion included in the rectangle R.

When counting the number of the cells according to the grid method, the operator must decide whether the cell is included entirely in the rectangle R or the cell is included partly in the rectangle R, which takes a long time for measurement.

It often occurs that cells having only a very small portion cut by the side of the rectangle R are mistaken for those entirely included in the rectangle R and cells having a very small portion included in the rectangle R are overlooked, which reduces the accuracy of measurement.

SUMMARY OF THE INVENTION

Accordingly, it is an object of the present invention to provide a corneal endothelial cell measuring instrument capable of reducing the necessity of operator's decision and operation to reduce time necessary for measurement and of achieving measurement in an improved measuring accuracy.

With the foregoing object in view, according to a first aspect of the present invention, a corneal endothelial cell measuring instrument comprises: a display means for displaying a corneal endothelial cell image picked up; a marking means for marking the centers of the respective cells in the corneal endothelial cell image displayed by the display means; a coordinate determining means for determining the coordinate value of the marked centers; a closed curve determining means for determining a closed curve formed by connecting the plurality of the marked centers; an area calculating means for calculating the area of a region enclosed by the closed curve by using output provided by the coordinate determining means; and a cell density calculating means for calculating cell density indicating the number of cells per unit area from the number of centers on the closed curve, the number of centers inside the closed curve and the area calculated by the area calculating means.

The necessity of operator's decision and operation is little, time necessary for measurement can be reduced and measuring accuracy can be improved.

According to a second aspect of the present invention, the closed curve determining means determines a maximum closed curve having a maximum area among closed curves which can be formed by connecting the marked centers.

Thus, measuring accuracy can further be improved.

According to a third aspect of the present invention, the corneal endothelial cell measuring instrument further comprises an informing means for informing that the continuation of the marking is necessary when the number of the marking cycles executed by the marking means is not greater than a predetermined number.

Thus, an accurate measurement can be prevented.

BRIEF DESCRIPTION OF THE DRAWINGS

The above and other objects, features and advantages of the present invention will become more apparent from the following description taken in connection with the accompanying drawings, in which:

FIGS. 4(a) and 4(b) are pictorial views of a corneal endothelial cell image displayed and a portion of the same, respectively, of assistance in explaining a method of calculating the number of cells according to a known grid method.

DESCRIPTION OF THE PREFERRED EMBODIMENTS

A preferred embodiment according to the present invention will be described hereinafter.

Figure 1:
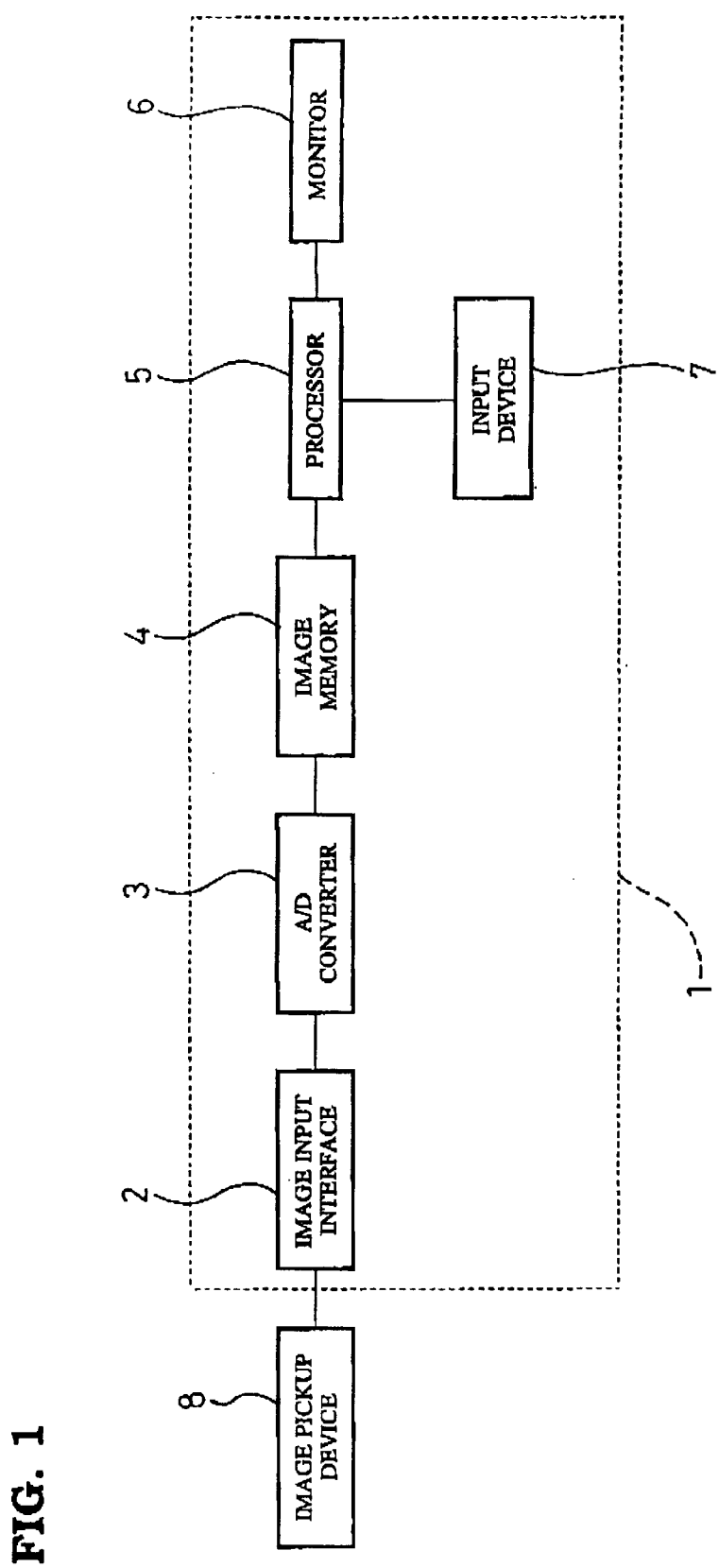
FIG. 1 is a block diagram of a corneal endothelial cell measuring instrument in a preferred embodiment according to the present invention.

Referring to FIG. 1, a corneal endothelial cell measuring instrument 1 in a preferred embodiment according to the present invention comprises an image input interface 2, an A/D converter 3, an image memory 4, a processor 5, a monitor 6 as a display means, and an input device 7, An image pickup device 8, such as a CCD camera, is connected to the image input interface 2. The corneal endothelial cell measuring instrument 1 receives an image signal representing an image of a corneal endothelium through the image input interface 2 from the image pickup device 8. When the image signal provided by the image pickup device 8 is an NTSC composite signal, the image input interface 2 is internally provided with a clamping circuit for preventing the variation of the DC level of a luminance signal extracted from the image signal, a synchronous separation circuit for separating a synchronizing signal from the image signal and the like. A system capable of photographing a corneal endothelium, of converting a picture image of the corneal endothelium into an image signal and of giving the image signal to the image input interface 2 may be used instead of the image pickup device 8.

The A/D converter 3 converts the luminance signal into a digital signal. The A/D converter 3 converts levels from a black level to a white level indicated by the image signal into digital values. The image memory 4 stores a digital image signal provided by the A/D converter 3, and the processor 5 makes the monitor 6 display an image represented by the stored digital image signal.

The input device 7 comprises a mouse, a track ball or the like. The operator uses the input device 7 to mark the centers of any cells in the corneal endothelial cell image displayed on the monitor 6. The processor 5 marks the centers of cells displayed on the monitor 6 with a dot according to a signal entered by the input device 7 and finds the coordinate value of the marks.

The processor 5 forms a closed curve enclosing a region having the greatest area among those of regions enclosed by closed curves connecting the plurality of marked centers, i.e., a closed curve enclosing a region so that all the marked centers lie in the enclosed region or on the closed curve. This specific closed curve will be referred to as the "maximum closed curve". The processor 5 calculates the area S of the region enclosed by the maximum closed curve by using the coordinate value of the marks.

Further, the processor 5 determines the number $N_{on}$ of the centers on the maximum closed curve and the number $N_{in}$ of the centers inside the maximum closed curve, and calculates the number N of the cells lying inside the maximum closed curve and cell density CD by using Expressions (1) and (2).

$$N=N_{in}+N_{on}/2 \qquad (1)$$

$$CD=N/S \qquad (2)$$

The operation of the corneal endothelial cell measuring instrument 1 will be explained hereinafter.

Figure 2A:
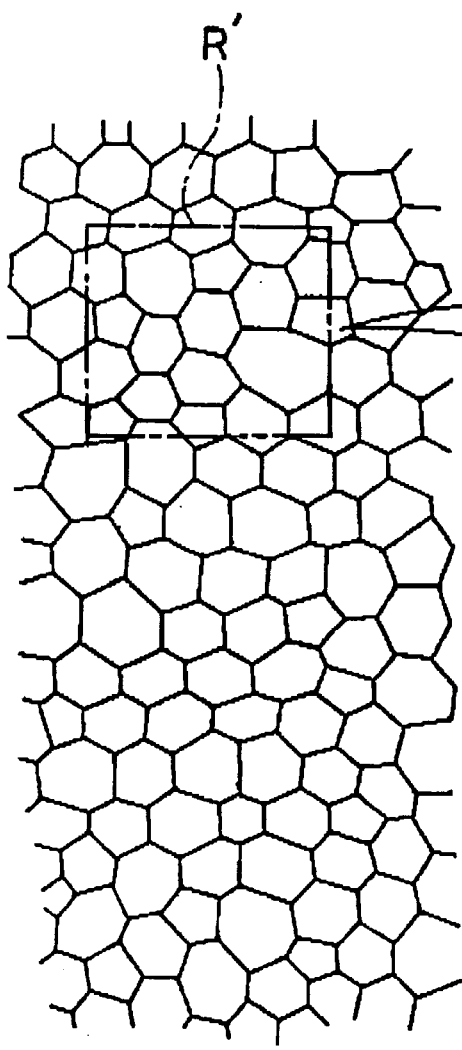
FIGS. 2(a) and 2(b) are pictorial views of a corneal endothelial cell image displayed on a screen of a monitor and a portion of the same, respectively.
Figure 2B:
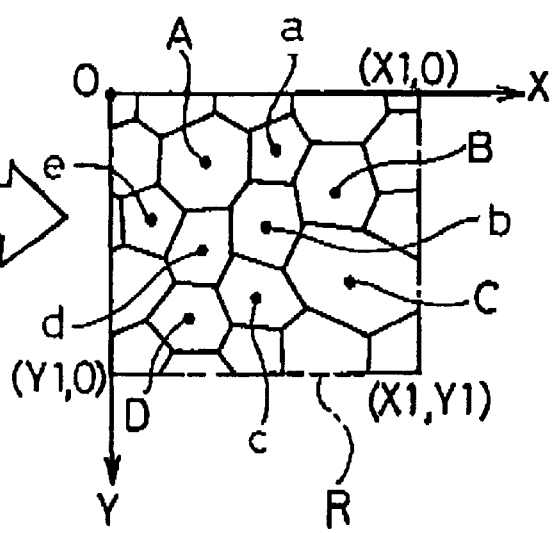

Suppose that a corneal endothelial cell image as shown in FIG. 2(a) is provided by the image pickup device 8. Then, a portion R' of the corneal endothelial cell image is displayed in an enlarged image as shown in FIG. 2(b) on the screen of the monitor 6. The operator operates the input device 7 watching the image displayed on the screen of the monitor 6, and marks the centers of the plurality of contiguous cells with a dot. In FIG. 2(b), the centers A, B, C, D, a, b, c, d and e of nine cells are marked.

After the completion of this marking operation, the processor 5 determines the coordinates of the marked centers on a coordinate system having its origin O at the upper left-hand corner of the screen of the monitor 6, an X-axis horizontally extending from the origin O and a Y-axis vertically extending from the origin O.

The coordinates (X, Y) are stored in the processor 5. The processor executes the following steps to determine a maximum closed curve.

The number of the cells having the marked centers must be greater than a predetermined number, such as eight, in order to achieve measurement in a satisfactory accuracy. If the operator tries to end the marking operation without marking eight or more cells, a warning is displayed on the screen of the monitor 6 to prompt the operator to continue the marking operation.

If the tested eye has a small cell density, it is possible that the number of cells displayed on the screen of the monitor 6 is less than the predetermined number and the number of cells that can be marked cannot exceed predetermined number. In such a case, the operator pushes a reset button, not shown, the display magnification of the monitor 6 is reduced automatically so that the number of cells that can be marked exceeds the predetermined number. Alternatively, when the reset button is depressed, a message to the effect that the display magnification should be reduced may be displayed to prompt the operator to reduce display magnification.

[Step 1]

A marked center at the uppermost leftmost position is selected as a first reference point A; that is, the distances between the origin O and the nine centers are calculated by using $r=(X^2+Y^2)^{1/2}$, and a center at the shortest distance r from the origin O is selected and stored as the first reference point A. Since the distance r between the origin O and the point reference point A is the shortest, the point A is regarded as the first reference point. If there are a plurality of points at the same shortest distance r from the origin O, the point having the smallest X-coordinate among the X-coordinates of the points having the same shortest distance r from the origin O is used as the first reference point.

Similarly, a point at the uppermost rightmost position with respect to a position (X1, 0) is selected as a second reference point B, a point at the lowermost rightmost position with respect to a position (X1, Y1) is selected as a third reference point C, and a point at the lowermost leftmost position with respect to a position (0, Y1) is selected as a fourth reference point D. Thus, the second reference point B, the third reference point C and fourth reference point D are determined.

[Step 2]

An operation for drawing a maximum closed curve is started from the first reference point A to the right. A search is made for points respectively having X-coordinates greater than that of the first reference point A. The five points B, C, a, b and c are selected. The gradient dY/dX of each of line segments connecting those points to the point A is calculated. The point a, located at one end of the line segment having the smallest gradient dY/dX, and the point B, located at one end of the line segment having the second smallest gradient dY/dX, are selected. It is decided that these points are the proposed "next points" for drawing and the rest are not regarded as "the next points".

Figure 3A:
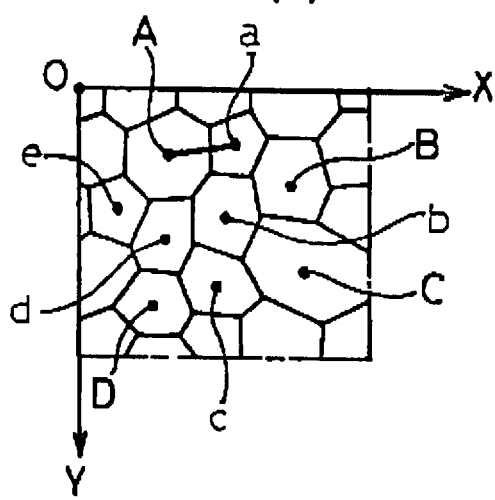
FIGS. 3(a) to 3(f) are pictorial views of assistance in explaining a procedure for forming a maximum closed curve by the corneal endothelial cell measuring instrument shown in the preferred embodiment in FIG. 1.

Subsequently, the respective lengths of the two line segments Aa and AB are compared. If the length of one of the line segments Aa and AB is equal to or greater than α times (α=2 in this embodiment) the length of the other line segment, the point on the shorter line segment is selected as the next point. The selected point and the point A is connected by a line segment to complete a drawing operation in step 2. If the length of one of the line segments is α times smaller than the length of the other line segment, the point on the line segment having the smallest gradient dY/dX is selected as the next point and a line segment connecting the selected point to the point A is drawn. In this,embodiment, the point a is the next point and a segment line Aa is displayed on the screen of the monitor 6 as shown in FIG. 3(a).

If the smallest gradient dY/dX is not greater than a predetermined reference value, the foregoing comparing step may be omitted, and a point on the line segment may be selected as the next point.

[Step 3]

Figure 3B:
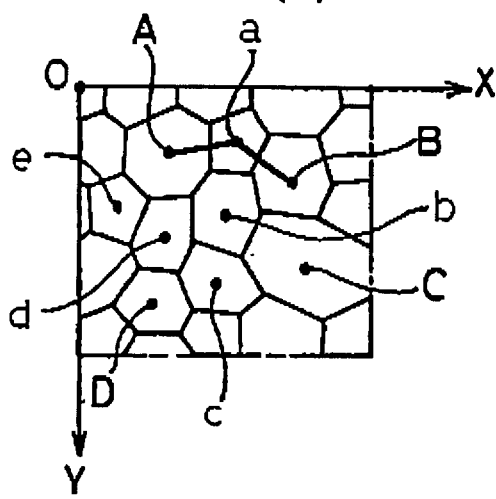

Similar to the determination of the next point with respect to the point A in step 2, the next point with respect to the point a is determined in step 3, and a line segment between the point a and the next point is drawn. In this case, the point B is selected as the next point and a line segment aB is displayed on the screen of the monitor 6 as shown in FIG. 3(b).

[Step 4]

The method of determining the next point is changed after the lines are extended to the point B, i.e., the second reference point. Since the point B is the uppermost rightmost point, the centers having Y-coordinate value greater than that of the point B are searched. In this case, the three points C, b and c are selected. The gradient dX/dY of each of line segments between the point B and those three points is calculated. The point C on the line segment having the largest gradient dX/dY and the point c on the line segment having the second largest gradient dX/dY are selected.

Figure 3C:
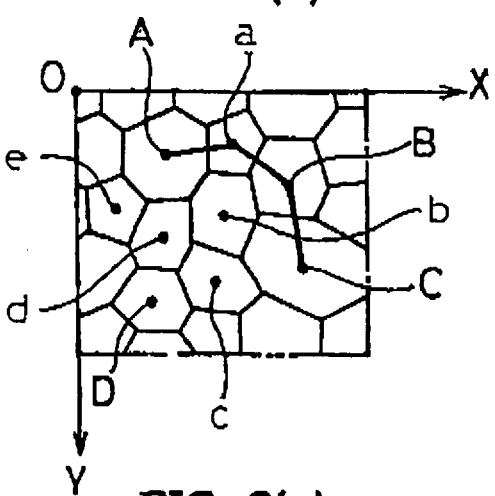

Subsequently, the respective lengths of the line segments BC and Bc are compared. If the length of one of those line segments is equal to or greater than α times (in this case α=2) the length of the other line segment, the point on the shorter line segment is selected as the next point. A line segment between the point B and the next point is drawn. If the length of one of those line segments is α times smaller than the length of the other line segment, the point pn the line segment having the largest gradient dX/dY is selected as the next point and a line segment between the point B and the next point is drawn. In this case, the point C is selected as the next point and a line segment BC is displayed on the screen of the monitor 6 as shown in FIG. 3(c).

If the largest gradient dX/dY is not smaller than a predetermined reference value, the step for comparison may be omitted and a point on-the line segment having the largest gradient dX/dY may be selected as the next point.

[Step 5]

After the line has been extended to the third reference point C, the method of determining the next point is changed. Since the point C is the lowermost rightmost point, the centers not yet selected and respectively having X-coordinate value smaller than that of the point C are searched. In this case, five points D, b, c, d and e are selected. The gradient dY/dX of each of line segments between the point C and those five points.is calculated. The point D on the line segment having the smallest gradient dY/dX and the point C on the line segment having the second smallest gradient dY/dX are selected.

Figure 3D:
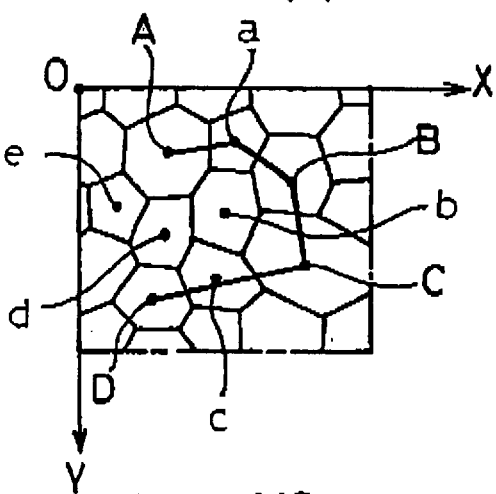

Subsequently, the respective lengths of the line segments CD and Cc are compared. If the length of one of those line segments is equal to or greater than α times (in this case α=2) the length of the other line segment, the point on the shorter line segment is selected as the next point. A line segment between the point C and the next point is drawn. If the length of one of those line segments is a times smaller than the length of the other line segment, the point on the line segment having the smallest gradient dY/dX is selected as the next point and a line segment between the point C and the next point is drawn. In this case, the point D is selected as the next point and a line segment CD is displayed on the screen of the monitor 6 as shown in FIG. 3(d).

If the smallest gradient dY/dX is not greater than a predetermined reference value, the step for comparison may be omitted and the point on the line segment having the smallest gradient may be selected as the next point.

[Step 6]

After the line has been extended to the fourth reference point D, the method of determining the next point is changed again. Since the point D is the lowermost leftmost point, the points not yet selected and respectively having Y-coordinate value smaller than that of the point D are searched. In this case, the four points b, c, d and e are selected. The gradient dX/dY of each of line segments between the point D and those four points is calculated. The point e on the line segment having the largest gradient dX/dY and the point d on the line segment having the second largest gradient dX/dY are selected.

Figure 3E:
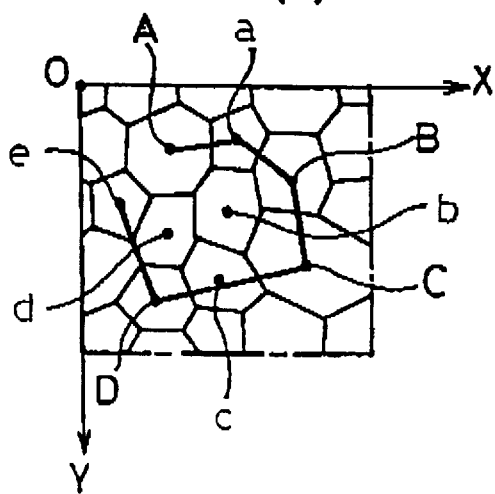

Subsequently, the respective lengths of the line segments De and Dd are compared. If the length of one of those line segments is equal to or greater than α times (in this case α=2) the length of the other line segment, the point on the shorter line segment is selected as the next point. A line segment between the point D and the next point is drawn. If the length of one of those line segments is α times smaller than the length of the other line segment, the point on the line segment having the largest gradient dX/dY is selected as the next point and a line segment between the point D and the next point is drawn. In this case, the point e is selected as the next point and a line segment De is displayed on the screen of the monitor 6 as shown in FIG. 3(e).

If the largest gradient dX/dY is not smaller than a predetermined reference value, the step for comparison may be omitted and the point on the line segment having the largest gradient may be selected as the next point.

[Step 7]

Figure 3F:
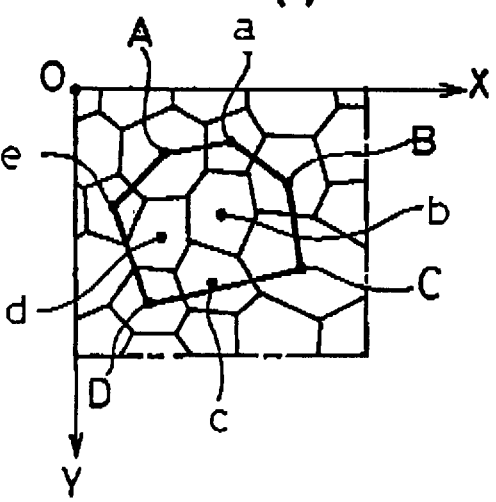

Similar to the determination of the next point with respect to the point D in step 6, the next point with respect to the point e is determined in step 7, and a line segment between the point e and the next point is drawn. In this case, the first reference point A is selected as the next point and a line segment eA is displayed on the screen of the monitor 6 as shown in FIG. 3(f).

After a maximum closed curve has thus been formed, the number N of cells inside the maximum closed curve is calculated by using Expression (1) and the cell density CD is calculated by using Expression (2) on the basis of the number $N_{on}$ of the point selected in the process of forming the maximum closed curve, i.e., the number of centers on the maximum closed curve, and the number $N_{in}$ of centers not selected in the process of forming the maximum closed curve, i.e., centers inside the maximum closed curve, In this case, $N$=3+6/2=6 (cells)

$CD$=6/$ (cells/mm$^2$)

Although all the cells having centers on the maximum closed curve are regarded as ½ cells in this embodiment (Expression (1)), the cells corresponding to the first to the fourth reference points, i.e., the cells corresponding to the points A, B, C and D in FIG. 3, may be regarded as ¼ cells in counting the cells.

Although this embodiment displays the maximum closed curve on the screen of the monitor 6, the maximum closed curve may be determined by only calculation and the indication of the same on the monitor may be omitted.

The corneal endothelial cell measuring instrument 1 is capable of determining only the cell density of a corneal endothelium and is incapable of determining mean cell area, standard deviation and the like. Therefore, when it is desired to determine mean area or the like, a known digitizing method or a known vertex input method may be used in combination with the corneal endothelial cell measuring instrument, and measurements may be displayed on the screen of the monitor 6.

Although the invention has been described in its preferred form with a certain degree of particularity, obviously many changes and variations are possible therein. It is therefore to be understood that the present invention may be practiced otherwise than as specifically described herein without departing from the scope and spirit thereof.

What is claimed is:

1. A corneal endothelial cell measuring instrument comprising:

a display means for displaying a corneal endothelial cell image picked up;

a marking means for marking centers of the respective cells in the corneal endothelial cell image displayed by the display means;

a coordinate determining means for determining coordinate value of the marked centers;

a closed curve determining means for determining a closed curve formed by connecting the plurality of the marked centers;

an area calculating means for calculating the area of a region enclosed by the closed curve by using output provided by the coordinate determining means; and a cell density calculating means for calculating cell density indicating the number of cells per unit area, from the number of centers on the closed curve, the number of centers inside the closed curve and the area calculated by the area calculating means.

2. The corneal endothelial cell measuring instrument according to claim 1, wherein the closed curve determining means determines a maximum closed curve having a maximum area among closed curves which can be formed by connecting the marked centers.

3. The corneal endothelial cell measuring instrument according to claim 1, further comprising an informing means for informing that continuation of the marking is necessary when the number of the marking cycles executed by the marking means is not greater than a predetermined number.

4. The corneal endothelial cell measuring instrument according to claim 2, further comprising an informing means for informing that continuation of the marking is necessary when the number of the marking cycles executed by the marking means is not greater than a predetermined number.

* * * * *